United States Patent
Hu et al.

(10) Patent No.: US 11,415,497 B2
(45) Date of Patent: Aug. 16, 2022

(54) SHEAR BOX OF SHEAR RHEOLOGY EXPERIMENT OF A SOFT ROCK FOR SIMULATING THE COUPLING OF THE RAINFALL SEEPAGE AND BLASTING VIBRATION

(71) Applicant: Wuhan University of Science and Technology, Wuhan (CN)

(72) Inventors: Bin Hu, Wuhan (CN); Liyao Ma, Wuhan (CN); Jianlong Sheng, Wuhan (CN); Guangquan Zhang, Wuhan (CN); Shibing Huang, Wuhan (CN); Shuxiang Chang, Wuhan (CN); Jing Ding, Wuhan (CN); Ji Liu, Wuhan (CN)

(73) Assignee: WUHAN UNIVERSITY OF SCIENCE AND TECHNOLOGY, Wuhan (CN)

( * ) Notice: Subject to any disclaimer, the term of this patent is extended or adjusted under 35 U.S.C. 154(b) by 169 days.

(21) Appl. No.: 17/079,390

(22) Filed: Oct. 23, 2020

(65) Prior Publication Data
US 2021/0123842 A1 Apr. 29, 2021

(30) Foreign Application Priority Data

Oct. 25, 2019 (CN) .......................... 201911022745.7
Oct. 25, 2019 (CN) .......................... 201911022921.7

(51) Int. Cl.
*G01N 3/24* (2006.01)
*G01N 3/02* (2006.01)
*G01N 33/24* (2006.01)

(52) U.S. Cl.
CPC .................. *G01N 3/24* (2013.01); *G01N 3/02* (2013.01); *G01N 2203/0025* (2013.01); *G01N 2203/0058* (2013.01); *G01N 2203/0236* (2013.01)

(58) Field of Classification Search
CPC ...... G01N 3/303; G01N 15/088; G01N 11/00; G01N 3/20; G01N 3/18; G01N 3/313; G01N 2203/0025; G01N 2203/0058; G01N 2203/0236; B05C 5/002
See application file for complete search history.

(56) References Cited

U.S. PATENT DOCUMENTS

| 2017/0284911 | A1* | 10/2017 | Ni ............................. | G01N 3/10 |
| 2018/0031457 | A1* | 2/2018 | Jiang ...................... | G01N 33/24 |
| 2018/0128725 | A1* | 5/2018 | Du ........................... | G01N 3/24 |
| 2019/0011344 | A1* | 1/2019 | Zhou ....................... | G01N 3/10 |

* cited by examiner

*Primary Examiner* — Brandi N Hopkins
(74) *Attorney, Agent, or Firm* — Bayramoglu Law Offices LLC

(57) ABSTRACT

A shear box of shear rheology experiment of a soft rock for simulating the coupling of the rainfall seepage and blasting vibration includes an upper shear box, a lower shear box, a normally-loading indenter, a normally-loading cushion block and a test piece joint. The upper shear box is tightly connected to the lower shear box by a vertical roll. The vertical roll passes through the through holes at both sides of the upper shear box and is engaged with the lower shear box through female thread connection holes. The normally-loading indenter passes through a circular through hole and presses against the normally-loading cushion block. The first end of the test piece joint is installed into a water or gas outlet hole, and the second end of the test piece joint is directly mortised into a rock test piece.

7 Claims, 3 Drawing Sheets

SHEAR BOX OF SHEAR RHEOLOGY EXPERIMENT OF A SOFT ROCK FOR SIMULATING THE COUPLING OF THE RAINFALL SEEPAGE AND BLASTING VIBRATION

CROSS REFERENCE TO THE RELATED APPLICATIONS

This application is based upon and claims priority to Chinese Patent Applications No. 201911022921.7, and No. 201911022745.7, both filed on Oct. 25, 2019, the entire contents of which are incorporated herein by reference.

TECHNICAL FIELD

The present application relates to a shear box, and specifically, to a shear box of shear rheology experiment of a soft rock for simulating the coupling of the rainfall seepage and blasting vibration.

BACKGROUND

Weak intercalation (a kind of soft rock) is an important structural form of shear sliding collapse failure of the slope in open-pit mining, and its mechanical property of shear rheology is one of the most important factors influencing the slope stability. In the field of geotechnical engineering, the shear rheology properties of rock masses have a significant impact on the long-time safety and stability of some major projects. In order to simulate and predict the long-time variation situation of the strength properties of the weak intercalation under natural conditions, it is the simplest and most effective methods to obtain the parameters of mechanical properties of the soft rock under different conditions by indoor shear rheology experiments at present.

Currently, the core technical difficulty in the development of a system of shear rheology experiment, which researches a soft rock for simulating the coupling of the rainfall seepage and blasting vibration, lies in the design and machining of the shear boxes. The shear box must not only be able to maintain the sealing of the shear box when high-pressure water or gas is injected, the sealing property must also not be affected under the condition of a repeating vibration load being applied. Generally, the problems regarding the existing shear boxes for the shear rheology experiment of a rock are as follows:

(1) When high-pressure water is injected into the shear box in a manner of radial flow, only a single hole is used for the injection of the high-pressure water, and the test piece joint inserted into the rock test piece is molded integrally with the normally-loading cushion block, it is tedious to disassembling the rock test pieces after a set of tests being completed, which affects the efficiency of the tests.

(2) During the experiments, the rock test pieces can be seeped by high-pressure water to increase the water content, it is impossible to dry the test pieces quickly; therefore, it is difficult to simulate the process of wetting and drying cycles of the rock test pieces under natural conditions.

(3) The dimension of the cavity in the shear box for placing the rock test pieces is invariable, a certain backlash would occur when the rock test pieces are placed into the cavity, while the existed backlash would cause deflection of the rock test pieces during the shearing process, thus affecting the accuracy of the test results.

(4) Sliding friction will occur between the upper shear box and lower shear box during the shearing process, which could not only create unnecessary energy dissipation, but what is more important is that the measured shear resistance of the rock test pieces is greater than the actual shear resistance. How to depress the influence of the friction force upon the test results is an urgent problem to be solved.

(5) Applying cyclic vibration load during the process of shear rheology experiment can well simulate the influence of blasting vibration on the test pieces under actual working conditions, however, currently there is no a test equipment for applying cyclic vibration load to the test pieces during the process of shear rheology experiment, and how to reform the shear box accordingly is an innovative problem.

SUMMARY

The present application aims to overcome the above defects existing in prior art by providing a shear box of shear rheology experiment of a soft rock for simulating the coupling of the rainfall seepage and blasting vibration, which can withstand high water or gas pressure, has a higher test accuracy and efficiency, and can conveniently and quickly realize the wetting and drying cycle of the test pieces, and furthermore, it can also provide suitable members for the device applying the cyclic vibration loads.

In order to realize the above purpose, the present application provides a technical solution in which a shear box of shear rheology experiment of a soft rock for simulating the coupling of the rainfall seepage and blasting vibration is provided which comprises at least an upper shear box, a lower shear box, a normally-loading indenter, a normally-loading cushion block and test piece joints;

The upper shear box is provided with an upper top plate and an upper shear body, and the upper top plate and is fastened and connected with the upper shear body by hexagon fillister head socket screws; the lower shear box is provided with a lower shear body and a lower base plate, the lower shear body is fastened and connected with the lower base plate by hexagon fillister head socket screws;

The upper shear box is tightly connected with the lower shear box by a vertical roll, the upper shear box is provided with through holes at both sides thereof, the lower shear box is provided with female thread connection holes at both sides thereof, the vertical roll passes through the through holes at both sides of the upper shear box and engages with the lower shear box through the female thread connection holes, and vertical roll is movable within the range of the through holes at both sides of the upper shear box during the shearing test; after the upper shear box and the lower shear box are tightly connected with each other, a cuboid cavity is formed in the inner walls of the upper shear body and the lower shear body, in which the rock test pieces are placed;

The upper top plate is provided with a circular through hole in the middle thereof, the normally-loading indenter passes through the circular through hole and presses against the normally-loading cushion block, the normally-loading indenter is provided with a top groove for mortising connection with the spherical universal indenter of the normal actuator so as to apply a normal load, the normally-loading indenter is provided with a lower groove at the lower part thereof for connecting with the normally-loading cushion block, the normally-loading cushion block has a protruding shape, where the head of the protruding shape is embedded into the lower groove of the normally-loading indenter, the shoulders of the normally-loading cushion block both contact with the upper top plate, and sides of the normally-loading cushion block contact with the inner wall of the upper shear body;

The normally-loading indenter is provided with a water or gas inlet channel communicating with the outside, the water or gas inlet channel extends downward vertically in the normally-loading indenter and into the normally-loading cushion block, then is transformed into a horizontal water or gas channel in the normally-loading cushion block, both ends of the horizontal water or gas channel are blocked up with hexagonal socket plugs, three water or gas outlet holes are provided at equal intervals at the lower part of the horizontal water or gas channel, test piece joints are installed into the three water or gas outlet holes, and the other ends of the three test piece joints are directly mortised into the rock test pieces;

A flat groove is provided outside of the cuboid cavity and at the junction of the upper shear box and the lower shear box, such a flat groove is used to avoid damage to the shear plane of the rock test piece, and a water or gas outlet channel for communicating with the outside of the shear box is provided in the flat groove;

The upper shear body is provided with a push screw and a pre-clamping plate on the same side as a tangential dynamic load actuator. The push screw passes through the upper shear body against the pre-clamping plate, and the push screw is twisted for pushing the pre-clamping plate and the rock test piece so as to make the rock test piece closely fit the upper shear body on the other side;

A movable sliding plate is provided above the upper top plate. A standard spring washer and a plain washer are arranged between the movable sliding plate and the upper part of the vertical roll.

Three O-ring seals of different specifications are provided between the upper top plate and the normally-loading indenter for sealing between the upper top plate and the normally-loading indenter, one sealing tape is provided between the bottom of the normally-loading indenter and the normally-loading cushion block for the sealing between the normally-loading indenter and the normally-loading cushion block, in order to prevent the high-pressure water or gas from leaking from the contact between the normally-loading indenter with the upper top plate, the normally-loading indenter and the normally-loading cushion block; rectangular sealing tapes are provided between the upper top plate and the upper shear body, between the lower shear body and the lower base plate, and along the circumference of the flat groove.

The three water or gas outlet holes have test piece joints installed therein, the water or gas outlet holes and the test piece joints each are formed with chamfers, and the contact between the test piece joint and the water or gas outlet hole is provided with annular joint sealing ring for sealing of the high-pressure water or gas.

Further, there are large ball rows, ball baffles and fastening screws on both sides of the lower shear body, the large ball row being used to reduce the friction force between the upper shear box and the lower shear box, the ball baffle is fastened onto the lower shear body through the fastening screws.

Further, there are small ball rows between the movable sliding plate and the upper top plate, the small ball row being used to transform the sliding friction between the movable sliding plate and the upper top plate into a rolling friction, thus reducing the friction force between the movable sliding plate and the upper top plate.

Further, there is a sliding roller row below the lower base plate, the sliding roller row being provided with roller row baffles and two layers of, i.e., the upper and lower layers of roller row plates, and the two layers of roller row plates are provided with orderly arranged ball holes in which the balls are placed, the sliding roller row is provided with rectangular holes in the middle thereof, and the roller row baffles are fastened onto the lower base plate for limiting the range of movement of the sliding roller rows; during the test, the sliding roller row turns the sliding friction between the lower base plate and the contact parts below into a rolling friction so as to reduce the system friction force and unnecessary energy consumption.

A grating ruler is arranged on the outer side of the shear box along the shearing direction for measuring the shear displacement.

The present application provides that, when simulating the shear rheology experiment of a soft rock, a cylindrical hole is preformed in the cuboid rock test piece which has a bore diameter greater than the outer diameter of the test piece joint, then during the test, glue is employed for bonding between the test piece joint and the wall of the cylindrical hole on the rock test piece.

When the shear box of rheology experiment of the present application is used, one end of the water or gas inlet channel is coupled with a plunger pump and power accumulator which can provide steady high-pressure water, and before water is pumped, a hexagonal socket plug is used to block up the inlet at one side of the water or gas inlet channel, thus achieving one-sided water intake. One end of the water or gas outlet channel connects with a flow metering system, where a great flow metering system or small flow metering system can be adopted for the flow metering system, the great flow metering system utilizes a flow meter to measure the amount of water seepage while the small flow metering system utilizes an electronic balance to meter the amount of water seepage. Here, both the water inlet end and the water outlet end are provided with water-pressure sensors for monitoring the water pressure.

The shear box of rheology experiment according to the present application may also connect with an air compressor pump at one end of the water or gas inlet channel, which air compressor pump is coupled with a micro pneumatic servo control system, the gas outlet end of the air compressor pump is provided with a barometer, and the micro pneumatic servo control system can automatically adjust the air pressure based on the magnitude of air pressure.

According to the present application, the sliding roller row at the bottom of the lower shear box is provided with a rectangular hole in the middle thereof, thus a space is reserved for arranging an actuator in the normal direction of the lower part of the shear box for applying cyclic vibration load.

The shear box of rheology experiment according to the present application has the following beneficial effects compared with the prior art:

(1), by pre-forming three cylindrical holes having a bore diameter greater than the outer diameter of the test piece joint at equal interval on the cuboid rock test piece, the present application can well make the entire rock test piece quickly seeped by the high-pressure water or gas, thus improving the test efficiency.

(2), the assembly of the test piece joint and the normally-loading cushion block of the present application is simple and easy, and it is sufficient to use glue for bonding between the test piece joint and the rock test piece, the test piece joint is replaced after each set of tests is completed, which is convenient and quick, and can improve the test efficiency very well.

(3), the water or gas inlet channel of the present application can not only carry out the shear rheology experiment of a soft rock under high water-seepage pressure, but also directly air-dry the rock test piece to continue with the tests while the rock test pieces are not disassembled from the shear box, which can well simulate the rheological effect of the rock test piece under the action of wetting and drying cycles.

(4), according to the present application, a pre-clamping plate is arranged at a side of the upper shear box, which can be pushed by twisting a push screw before performing the shear rheology experiment, so that the rock test pieces are in close contact with the upper shear body, thus effectively avoiding the situation in which the accuracy of the test results is influenced due to the rock test pieces occurring deflection during the shearing process since the rock test pieces are not in close contact with the shear body.

(5), according to the present application, a small ball row is arranged between the upper top plate and the movable sliding plate, a large ball row is arranged between the upper shear box and the lower shear box, and a sliding roller row is arranged at the bottom of the lower shear box, in such a way that the sliding friction between the above parts is turned into a rolling friction which can effectively depress the system friction force and unnecessary energy consumption.

(6), according to the present application, the sliding roller row at the bottom of the lower shear box is provided with a rectangular hole in its middle part, the purpose of which is to facilitate arranging an actuator in the normal direction of the lower part of the shear box which could apply cyclic vibration load; the design of a rectangular hole is very simple, however, there is currently no a test equipment disclosed in the world that applies cyclic vibration load to the test pieces during the shear rheological test to simulate the effect of blasting vibration; the design of such a rectangular hole is an innovative part to reform the shear box, and the cyclic vibration load applied during the process of shear rheology experiment can well simulate the impact of blasting vibration on the rock test pieces under actual working conditions.

In the above drawings: 1—normally-loading indenter, 2—water or gas inlet channel, 3—vertical roll, 4—movable sliding plate, 5—upper top plate, 6—O-ring seal, 7—hexagonal socket plug, 8—normally-loading cushion block, 9—test piece joint, 10—flat groove, 11—joint sealing ring, 12—sliding roller row, 13—ball, 14—lower base plate, 15—lower shear body, 16—water or gas outlet channel, 17—sealing tape, 18—push screw, 19—large ball row, 20—fastening screw, 21—ball baffle, 22—roller row baffle, 23—rectangular sealing tape, 24—upper shear body, 25—through hole, 26—ball hole, 27—pre-clamping plate, 28—rectangular hole, 29—small ball row, 30—hexagon fillister head socket screw, 31—plain washer, 32—standard spring washer, 33—rock test piece

DETAILED DESCRIPTION OF THE EMBODIMENTS

The shear box of the present application will be further described below in conjunction with the drawings and specific embodiments. The embodiments are implemented based on the technical solution of the present application, and however, the protection scope of the present application is not limited to the following embodiments.

Embodiment 1: the present application provides a shear box of shear rheology experiment of a soft rock for simulating the coupling of the rainfall seepage and blasting vibration, and the structure of the shear box is as shown in FIGS. 1-5. The shear box of the present application comprises at least an upper shear box, a lower shear box, a normally-loading indenter 1, a normally-loading cushion block 8, and a test piece joint 9.

Figure 1:
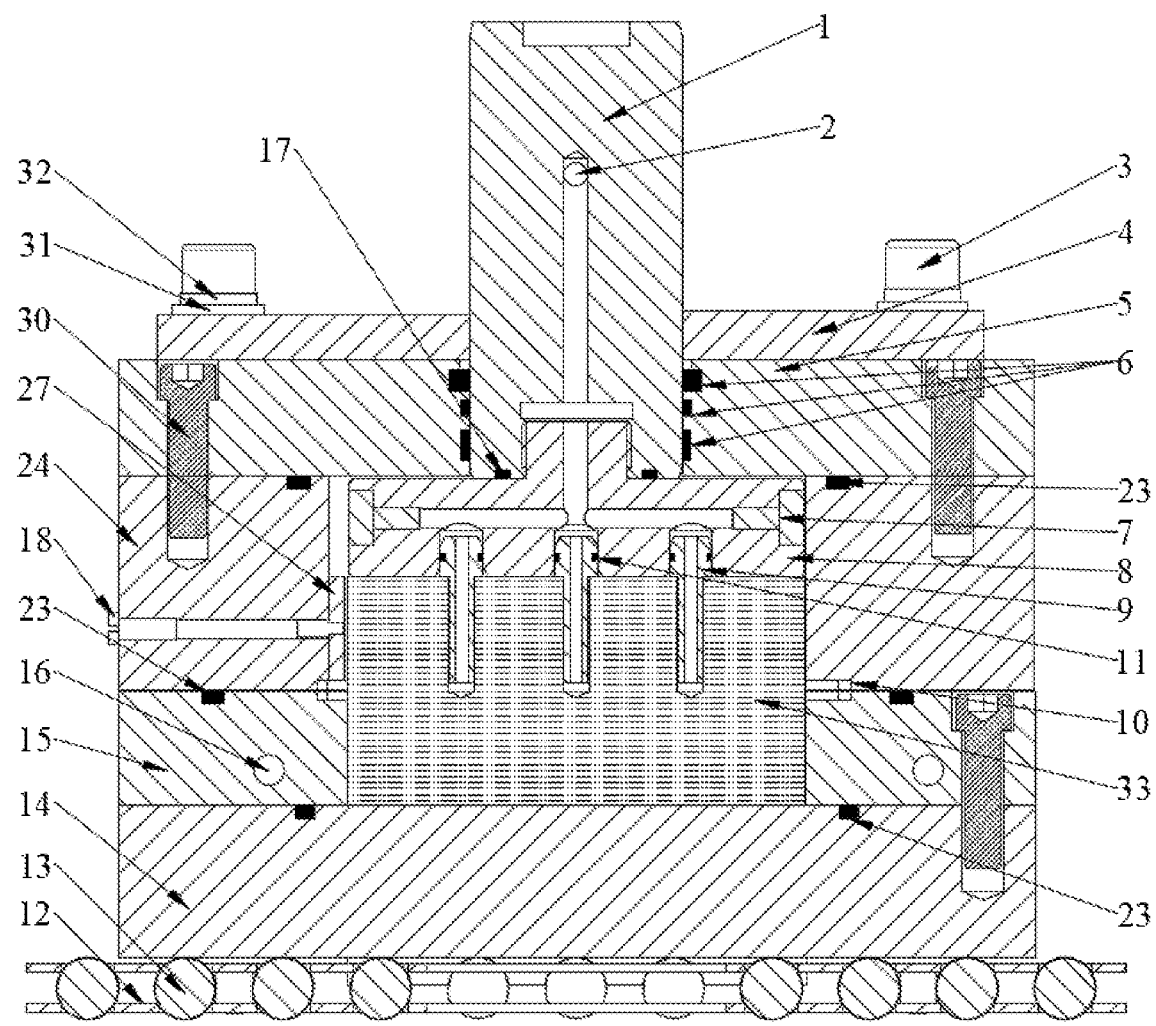
FIG. 1 is a schematic view of the front cross-sectional structure of the shear box of the present application.

Referring to FIG. 1, the upper shear box is provided with an upper top plate 5 and an upper shear body 24, and the upper top plate and is fastened and connected with the upper shear body by hexagon fillister head socket screws 30; the lower shear box is provided with a lower shear body 15 and a lower base plate 14, the lower shear body is fastened and connected with the lower base plate by hexagon fillister head socket screws; the upper shear box is tightly connected with the lower shear box by a vertical roll 3, the upper shear box is provided with through holes 25 at both sides thereof, the lower shear box is provided with female thread connection holes at both sides thereof, the vertical roll passes through the through holes at both sides of the upper shear box and engages with the lower shear box through the female thread connection holes, during the test process, a tangential static load actuator pushes the lower shear box and the vertical roll 3 connected to the lower shear box, then the vertical roll will move within the range of the through holes 25 on both sides of the upper shear box, while the upper shear body 24 and the upper top plate 5 remain stationary; after the upper shear box and the lower shear box are tightly connected with each other, a cuboid cavity is formed in the inner walls of the upper shear body 24 and the lower shear body, in which the rock test pieces 33 are placed.

The upper top plate 5 is provided with a circular through hole in the middle thereof, the normally-loading indenter 1 passes through the circular through hole and presses against the normally-loading cushion block 8, the normally-loading indenter is provided with a top groove for mortising connection with the spherical universal indenter of the normal actuator so as to apply a normal load, the normally-loading indenter is provided with a lower groove at the lower part thereof for connecting with the normally-loading cushion block; the normally-loading cushion block has a protruding shape, where the head of the protruding shape is embedded into the lower groove of the normally-loading indenter, the shoulders of the normally-loading cushion block both contact with the upper top plate 5, and sides of the normally-loading cushion block contact with the inner wall of the upper shear body 24.

Figure 2:
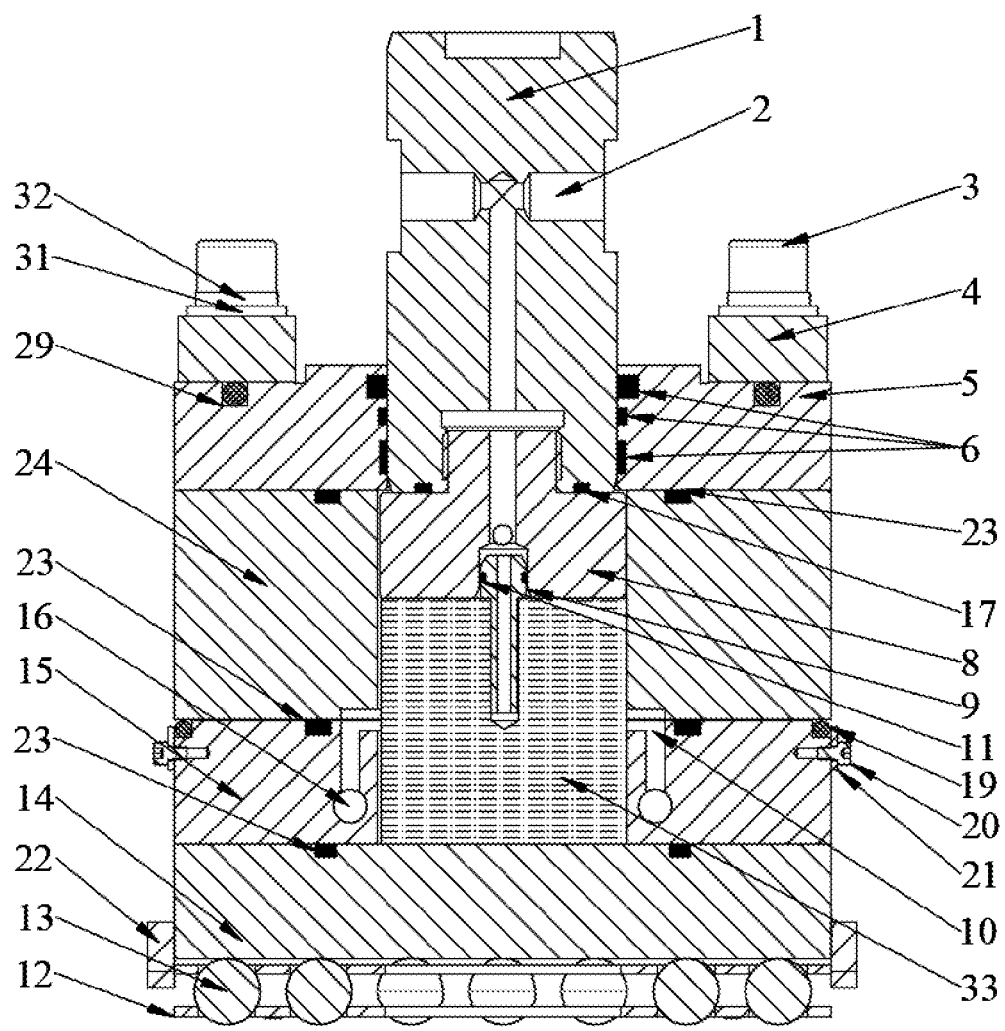
FIG. 2 is a schematic view of the side cross-sectional structure of the shear box of the present application.

The normally-loading indenter is provided with a water or gas inlet channel 2 communicating with the outside, referring to FIG. 2, the water or gas inlet channel has two water or gas inlet port, the water or gas inlet channel 2 extends downward vertically in the normally-loading indenter 1 and into the normally-loading cushion block 8, then is transformed into a horizontal water or gas channel in the normally-loading cushion block, both ends of the horizontal water or gas channel are blocked up with hexagonal socket plugs 7, three water or gas outlet holes are provided at equal intervals at the lower part of the horizontal water or gas channel, non-reusable but removable test piece joints 9 are installed into the three water or gas outlet holes respectively, the test piece joint and the water or gas outlet holes are each formed with chamfers, and the contact of the test piece joint with the water or gas outlet hole is provided with a joint sealing ring 11 for sealing from the high-pressure water or gas, and the other ends of the three test piece joints 9 are directly mortised into the cuboid rock test pieces.

Three O-ring seals 6 of different specifications are provided between the upper top plate and the normally-loading indenter for sealing between the upper top plate 5 and the normally-loading indenter 1, one sealing tape 17 is provided at the bottom of the normally-loading indenter for sealing between the normally-loading indenter 1 and the normally-loading cushion block 8, in order to prevent the high-pressure water or gas from leaking from the contact between the normally-loading indenter with the upper top plate, the normally-loading indenter and the normally-loading cushion block; rectangular sealing tapes 23 are provided at the contact of the upper top plate 5 with the upper shear body 24, between the lower shear body 15 and the lower base plate 14, and along the circumference of the flat groove 10.

The water or gas inlet channel 2 has inlets at both ends, before inputting high-pressure water or gas toward the normally-loading indenter 1, the inlet at one side of the water or gas inlet channel 2 is blocked up using a hexagonal socket plug, then the high pressure water passes through the normally-loading indenter 1 and the normally-loading cushion block 8 along the inlet at the other side, finally into the rock test piece 33 through the test piece joint 9. Since the test piece joint is non-reusable, the test piece joint needs to be replaced after the completion of each set of the tests. The high pressure water seeps through the rock test piece and then flows into the flat groove 10. The flat groove is a groove of a certain height and width provided at the connection of the upper shear body and the lower shear body encircling the cuboid cavity, which groove can prevent the shear plane of the rock test piece from being damaged during the shearing process, and the flat groove is provided with a water or gas outlet channel 16 communicating with the outside of the shear box, and the outer side of the flat groove is provided with a rectangular sealing tape 23. At the same time, In order to dry the rock test pieces quickly during the tests, the water or gas inlet channel 2 can also be coupled with an air compressor pump for inputting dry air to air-dry the rock test piece, so as to reduce the water content of the rock test pieces.

According to the present application, the rock test piece 33 is formed into cuboid test pieces which will be placed into the cuboid cavity when performing the shear rheology experiment. Referring to FIGS. 1 and 2, According to the present application, the upper shear body 24 is provided with a pre-clamping plate 27 and a push screw 18 at the same side as a tangential dynamic load actuator, for pushing the rock test pieces, that is to say, on the left side of the rock test piece 33 in FIG. 1, the push screw passes through the upper shear body against the pre-clamping plate, and before the start of the test, we should try to twist the push screw to push the pre-clamping plate and the rock test piece, so that the rock test piece closely fits to the upper shear body on the other side. At the same time, in order to decrease the friction force of the upper shear body 24 and the lower shear body 15 during the shearing process, a large ball row 19, a ball baffle 21 and fastening screws 20 are arranged on the outside of the lower shear body along the shearing direction, and the ball baffle is fastened to the lower shear body by the fastening screws.

Figure 3:
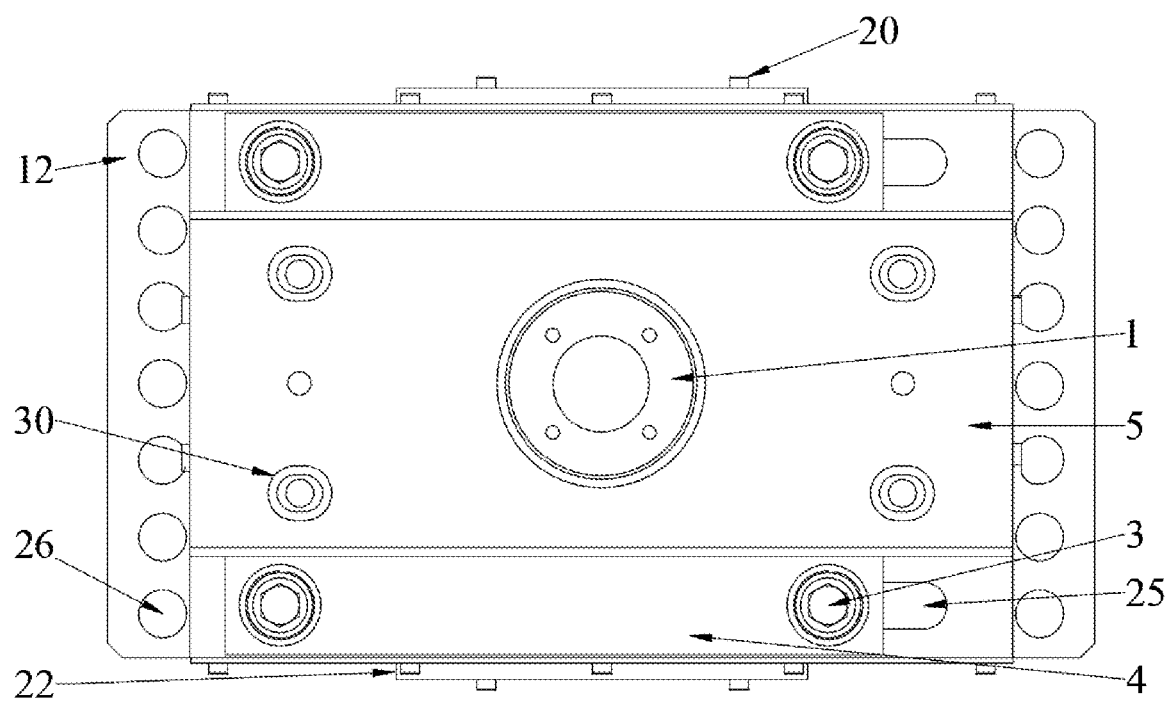
FIG. 3 is a schematic top view of the structure of the shear box of the present application.
Figure 4:
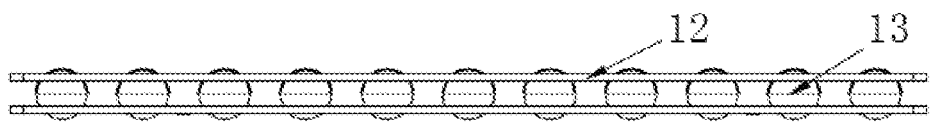
FIG. 4 is a schematic front view of the structure of the sliding roller row at the bottom of the shear box of the present application.
Figure 5:
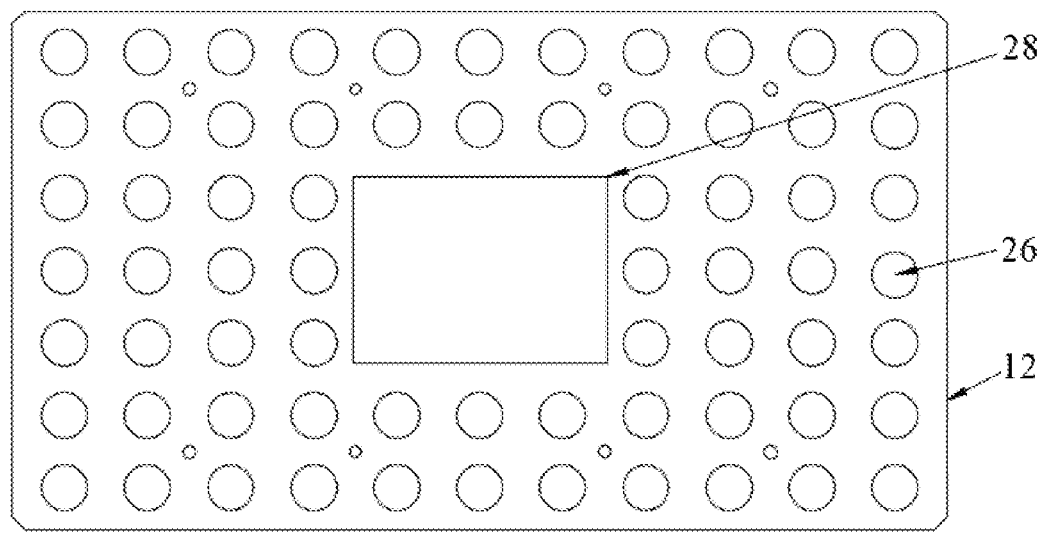
FIG. 5 is a schematic top view of the structure of the sliding roller row at the bottom of the shear box of the present application.

According to the present application, a movable sliding plate is provided above the upper top plate 5. Referring to FIGS. 1, 2 and 3, a standard spring washer 32 and a plain washer 31 are placed between the movable sliding plate and the upper part of the vertical roll 3. In order to decrease the system friction force and depress unnecessary energy consumption, a small ball row 29 is arranged between the movable sliding plate and the upper top plate 5, such a small ball row 29 is used to turn the sliding friction between the movable sliding plate and the upper top plate into a rolling friction, thus decreasing the friction force between the movable sliding plate and the upper top plate.

Referring to FIGS. 2, 3, 4 and 5, a sliding roller row 12 and a roller row baffle 22 are arranged below the lower base plate 14 of the lower shear box, the sliding roller row is provided with two layers of roller row plates, i.e., upper layer of roller row plates and lower layer of roller row plates, the roller row plate is formed with ball holes 26 arranged orderly, balls 13 are placed into the ball holes; the roller row baffle 22 is fastened to either side of the lower base plate 14 by fastening screws 20, the roller row baffle defines the range of movement of the sliding roller row 12, and also keeps the relative position of the sliding roller row to the lower shear box constant; one rectangular hole 28 is opened at the central portion of the sliding roller row, such a rectangular hole is reserved for arranging an actuator along the normal direction to the lower part of the shear box, which actuator is used to apply cyclic vibration load.

According to the present application, a grating ruler is arranged on the outside of the shear box along the shearing direction for the measuring of the shear displacement (not shown in the drawings).

The shear box of the present application is used to perform shear rheology experiment of a soft rock simulating the coupling of the rainfall seepage and blasting vibration, and its specific steps are as follows:

(1) preparing rock test pieces 33 having a cuboid shape with a length of 150 mm in the shearing direction and a length of 75 mm along the other two directions; and low-strength materials such as carbonaceous mud shale are used for the test pieces.

When the rock test piece 33 has been cut into the required shape, it is required to drill three cylindrical holes with a diameter of 4 mm and a depth of 37.5 mm at equal intervals on the center line parallel to the shearing direction on the top part of the rock test piece, and clean the inside of the cylindrical holes.

(2) installing the lower shear box, the sliding roller row 12 and the rectangular sealing tape 23 in the lower shear box, screwing up the hexagon fillister head socket screw 30 to ensure the close contact of the lower shear body 15 with the lower base plate 14; thereafter putting the rock test piece 33 into the cuboid cavity of the lower shear box; then installing the upper shear body 24 and the remaining rectangular sealing tapes 23. Here, the assembly should be reasonable in such a way that the verticality and parallelism of the upper shear body and the lower shear body can be ensured;

assembling the upper top plate 5 and the normally-loading indenter 1, at the same time mounting the O-ring seal 6 and the sealing tape 17 to ensure that the lower part of the normally-loading indenter is parallel with the bottom of the upper top plate; then embedding the protruding-shaped head of the normally-loading cushion block 8 into the lower groove of the normally-loading indenter; mounting the test piece joint 9 onto the normally-loading cushion block 8, here, appropriate force should be used during mounting to ensure the close contact of the test piece joint with the normally-loading cushion block, at the same time screwing up the hexagonal socket plug 7 to close the two ends of the horizontal water or gas channel inside the normally-loading cushion block; applying glue evenly onto the outer wall of the test piece joint 9 and inner wall of the cylindrical holes of the rock test piece. Aligning the test piece joint with the cylindrical hole in the rock test piece, lowering and mounting the normally-loading indenter 1, the upper top plate 5 and the normally-loading cushion block 8, screwing up the hexagon fillister head socket screw 30 to ensure the close contact between the upper top plate 5 and the upper shear body 24. Finally, installing the movable sliding plate 4 and screwing up the vertical roll 3, so that the upper shear box is in close contact with the lower shear box.

(3) twisting the push screw 18 to push the pre-clamping plate 27 and the rock test piece to tightly abut against the upper shear body on the other side;

(4) putting the assembled shear box into a predetermined test station, connecting the water or gas inlet channel 2 to a water inlet pipe connected with a hydraulic loading system, connecting the water or gas outlet channel 16 to a water outlet pipe connected to a water-flow metering system; Then after checking whether each system works properly, conducting the shear rheology experiment of a soft rock;

(5) the rock test piece and the shear box don't need to be disassembled when the wetting-drying test is to be conducted, the water or gas inlet channel is coupled with an air compressor pump for inputting dry air to air-dry the rock test piece so as to reduce the water content in the rock test piece, in such a way that the test can be continued on the rock test piece during the air drying process, such a process can better simulate the rheological effect of rock test piece under the action of wetting and drying cycles;

(6) after the test, taking the sequence inverse to the installation sequence of step (2) to take out the tested rock test piece and clean the inside of the shear box.

The shear box according to the present application has a simple structure, and the installation between the test piece joint and the normally-loading cushion block is convenient and easy, and the test efficiency could be best improved; the present shear box can ensure the sealing of the high-pressure water or gas and rapid wetting and drying cycle for the rock test pieces, and the friction force in the shearing process is small, and the shearing test results coincide with the actual situation.

What is claimed is:

1. A shear box of a shear rheology experiment of a soft rock for simulating a coupling of a rainfall seepage and a blasting vibration, comprising an upper shear box, a lower shear box, a normally-loading indenter, a normally-loading cushion block, and a test piece joint; wherein:

the upper shear box is provided with an upper top plate and an upper shear body, and the upper top plate is fastened and connected to the upper shear body by first hexagon fillister head socket screws; the lower shear box is provided with a lower shear body and a lower base plate, the lower shear body is fastened and connected to the lower base plate by second hexagon fillister head socket screws;

the upper shear box is tightly connected to the lower shear box by a vertical roll; through holes are provided at both sides of the upper shear box, and female thread connection holes are provided at both sides of the lower shear box; the vertical roll passes through the through holes at the both sides of the upper shear box and the vertical roll engages with the lower shear box through the female thread connection holes; the vertical roll is movable within a range of the through holes at the both sides of the upper shear box during a shearing test; after the upper shear box and the lower shear box are tightly connected to each other, a cuboid cavity is formed in an inner wall of the upper shear body and an inner wall of the lower shear body, and a rock test piece is placed in the cuboid cavity;

a circular through hole is provided in a middle of the upper top plate, the normally-loading indenter passes through the circular through hole and the normally-loading indenter presses against the normally-loading cushion block; the normally-loading indenter is provided with a top groove for mortising connection with a spherical universal indenter of a normal actuator to apply a normal load; a lower groove for connecting with the normally-loading cushion block is provided at a lower part of the normally-loading indenter; the normally-loading cushion block has a protruding shape, wherein a head of the protruding shape is embedded into the lower groove of the normally-loading indenter; both shoulders of the normally-loading cushion block contact with the upper top plate, and sides of the normally-loading cushion block contact with the inner wall of the upper shear body;

the normally-loading indenter is provided with a water or gas inlet channel communicating with an outside of the shear box; the water or gas inlet channel extends downward vertically in the normally-loading indenter and into the normally-loading cushion block, then the water or gas inlet channel is transformed into a horizontal water or gas channel in the normally-loading cushion block, and both ends of the horizontal water or gas channel are blocked up with hexagonal socket plugs; three water or gas outlet holes are provided at equal intervals at a lower part of the horizontal water or gas channel, a first end of the test piece joint is installed into each of the three water or gas outlet holes, respectively, and a second end of the test piece joint is directly mortised into the rock test piece;

a flat groove is provided at an outside of the cuboid cavity and the flat groove is located at a junction of the upper shear box and the lower shear box; the flat groove is configured to avoid damage to a shear plane of the rock test piece, and a water or gas outlet channel for communicating with the outside of the shear box is provided in the flat groove;

the upper shear body is provided with a push screw and a pre-clamping plate, and the push screw, the pre-clamping plate and a tangential dynamic load actuator are located on a first side of the upper shear body; the push screw passes through the upper shear body and against the pre-clamping plate, and the push screw is twisted to push the pre-clamping plate and the rock test piece to enable the rock test piece to tightly fit a second side of the upper shear body; and a movable sliding plate is provided above the upper top plate, and a standard spring washer and a plain washer are arranged between the movable sliding plate and an upper part of the vertical roll.

2. The shear box according to claim 1, wherein, three O-ring seals of different specifications are provided between the upper top plate and the normally-loading indenter for sealing the upper top plate and the normally-loading indenter; one sealing tape is provided between a bottom of the normally-loading indenter and the normally-loading cushion block for sealing the normally-loading indenter and the normally-loading cushion block, to prevent high-pressure water or gas from leaking from a contact between the normally-loading indenter with the upper top plate, the normally-loading indenter and the normally-loading cushion block; a first rectangular sealing tape is provided between the upper top plate and the upper shear body, a second rectangular sealing tape is provided between the lower shear body and the lower base plate, and a third rectangular sealing tape is provided along a circumference of the flat groove.

3. The shear box according to claim 1, wherein, the test piece joint is installed in each water or gas outlet hole of the three water or gas outlet holes, and the each water or gas outlet hole and the test piece joint are provided with chamfers, and a contact between the test piece joint and the each water or gas outlet hole is provided with an annular joint sealing ring for sealing high-pressure water or gas.

4. The shear box according to claim 1, wherein, a first ball row, a ball baffle and a fastening screw are provided on both sides of the lower shear body; the first ball row is configured to reduce a friction force between the upper shear box and the lower shear box, the ball baffle is fastened onto the lower shear body through the fastening screw.

5. The shear box according to claim 1, wherein, a second ball row is provided between the movable sliding plate and the upper top plate, and the second ball row is configured to transform a sliding friction between the movable sliding plate and the upper top plate into a rolling friction to reduce a friction force between the movable sliding plate and the upper top plate.

6. The shear box according to claim 1, wherein, a sliding roller row is provided under the lower base plate, and the sliding roller row is provided with roller row baffles, an upper roller row plate and a lower roller row plate; the upper roller row plate and the lower roller row plate are provided with orderly arranged ball holes, and balls are placed in the orderly arranged ball holes; rectangular holes are provided in a middle of the sliding roller row; the roller row baffles are fastened onto the lower base plate for limiting a range of movement of the sliding roller row; during the shearing test, the sliding roller row turns a sliding friction between the lower base plate and a contact part arranged under the lower base plate into a rolling friction to reduce a system friction force and an unnecessary energy consumption.

7. The shear box according to claim 1, wherein, a grating ruler is arranged on an outer side of the shear box along a shearing direction for measuring a shear displacement.

* * * * *